United States Patent [19]

Simond et al.

[11] Patent Number: 4,668,679

[45] Date of Patent: May 26, 1987

[54] AMINOETHYL-PYRIDINE AND PYRAZINE DERIVATIVES

[75] Inventors: Jacques A. L. Simond, Chamalieres; Patrick Carlier, Riom; André J. Monteil, Chatel-Guyon, all of France

[73] Assignee: Riom Laboratories C.E.R.M., Riom, France

[21] Appl. No.: 812,976

[22] Filed: Dec. 24, 1985

Related U.S. Application Data

[63] Continuation of Ser. No. 591,519, Mar. 20, 1984, abandoned.

[30] Foreign Application Priority Data

Mar. 22, 1983 [FR] France .................................. 8304690

[51] Int. Cl.$^4$ .................. C07D 401/06; C07D 403/06; A61K 31/495
[52] U.S. Cl. .................................. 514/252; 544/360; 544/357; 544/295; 544/124; 546/334; 546/281
[58] Field of Search ................ 546/281; 544/337, 360; 514/252

[56] References Cited

U.S. PATENT DOCUMENTS 4,358,455 11/1982 Atkinson et al. ............... 546/270 X
4,460,580 7/1984 Ostermayer et al. ........... 548/236 X
4,578,467 3/1986 Bonacchi et al. .................... 544/360

OTHER PUBLICATIONS

Derwent Abstract 12797w/08 of BE 820,242 16-Jan.-75.

*Primary Examiner*—Donald G. Daus
*Assistant Examiner*—William A. Teoli, Jr.
*Attorney, Agent, or Firm*—Abelman, Frayne, Rezac & Schwab

[57] ABSTRACT

The invention relates to compounds of the formula:

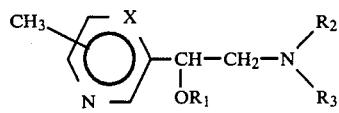

and pharmaceutically acceptable salts thereof, in which X represents either —CH= or —N=, $R_1$ represents an alkyl radical having 1 to 5 carbon atoms, $R_2$ represents hydrogen and $R_3$ is an alkyl radical having 1 to 5 carbon atoms, or $R_2$ and $R_3$, together with the nitrogen atom to which they are bonded, represent a heterocyclic radical, such as pyrrolidinyl, morpholino, 4-phenyl-piperazinyl, in which the phenyl radical can carry one or more substituents, such as a halogen atom, an alkyl or alkoxy radical having 1 to 5 carbon atoms or the trifluoromethyl radical, or represents 4-(2-pyrimidinyl)-piperazinyl, having anti-bronchoconstrictory properties.

2 Claims, No Drawings

AMINOETHYL-PYRIDINE AND PYRAZINE DERIVATIVES

This is a continuation of application Ser. No. 591,519 filed Mar. 20, 1984 now abandoned.

The present invention relates to new aminoethyl-pyridine or -pyrazine derivatives and to methods for their preparation.

More particularly the invention relates to (1-alkoxy-2-amino)ethyl-pyridine or -pyrazine derivatives of the general formula I:

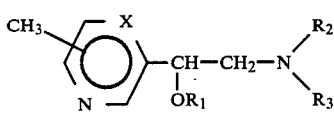

and pharmaceutically acceptable salts thereof, in which X represents either —CH= or —N=, $R_1$ represents an alkyl radical having 1 to 5 carbon atoms, $R_2$ represents hydrogen and $R_3$ is an alkyl radical having 1 to 5 carbon atoms, or $R_2$ and $R_3$ together with the nitrogen atom to which they are bonded represent a heterocyclic radical, such as pyrrolidinyl, morpholino, 4-phenylpiperazinyl, in which the phenyl radical may be substituted by one or more substituents, such as halogen, an alkyl or alkoxy radical having 1 to 5 carbon atoms or the trifluoromethyl radical, or represents 4-(2-pyrimidinyl)-piperazinyl.

The invention also relates to a pharmaceutical preparation containing the compounds of the formula (I) and their pharmaceutically acceptable salts, in particular in view of their valuable antibroncho-constrictory properties.

Compounds containing a 2-alkoxy-ethylamino sidechain are already known from the French Patents No. 1,385,772 and No. 1,404,442, where products are described of the general formula:

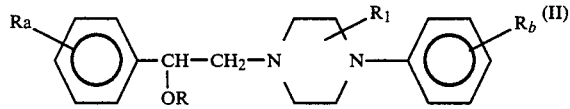

in which $R_a$ is halogen; $R_b$ is hydrogen, a lower alkyl or alkoxy radical or halogen, R is a lower alkyl radical and $R_1$ represents H or $CH_3$. These compounds are disclosed to have anti-inflammatory, hypotensive, diuretic or salidiuretic properties.

Compounds in which the phenyl radical (which is not bonded to the nitrogen) is replaced by an unsubstituted heterocyclic radical are known from British Pat. No. 1,551,993, where products are described of the formula:

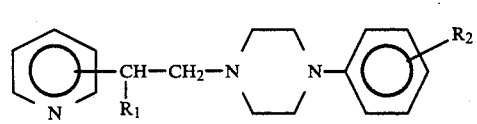

in which $R_1$ represents H, OH or a lower alkoxy radical; and $R_2$ represents H, a lower alkyl or alkoxy radical or halogen. Said compounds are described for their antihypertensive, antihistaminic and antibradykininic properties.

Compared with these groups of prior art products, the compounds according to the present invention have a pattern of biological activities which is either different or has a much greater intensity, leading to a much more favourable therapeutic index.

Compared with the compounds of structure III, the compounds of the formula I according to the invention are chemically characterised by the nitrogen atom of the heterocyclic radical being always in the 3-position relative to the bonding carbon, and the heterocyclic radical being substituted by a methyl radical.

Preferred compounds according to the invention are compounds of formula I, in which X represents —CH=, the methyl radical is in the 4-position, and the

moiety represents a 4-phenylpiperazinyl radical which is optionally substituted at the phenyl moiety.

The compounds of the invention may be prepared by any method known for the preparation of analogous compounds.

A general method for preparing the present compounds consists of a condensation of a compound of the formula IV

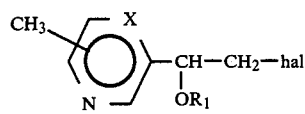

in which X and $R_1$ have the meanings assigned above and hal means a halogen atom, preferably bromo or chloro, with an amine of the formula V

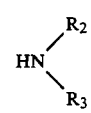

or a reactive derivative thereof, in which hydrogen has been replaced by a metal or metal derivative, such as for example sodium or lithium, in which $R_2$ and $R_3$ have the meanings assigned above.

A preferred process according to the invention is a process in two steps starting from 3-vinylpyridine or 2-vinylpyrazine substituted by a methyl radical, in accordance with the following equation:

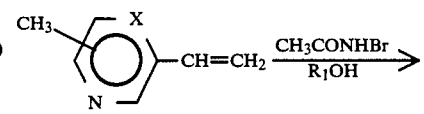

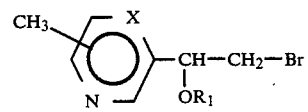

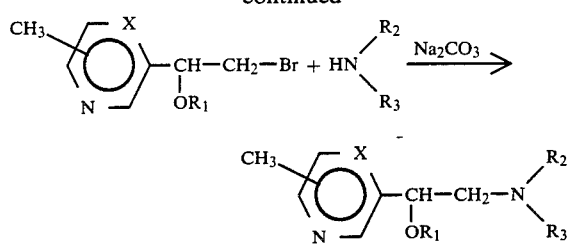

In the first stage, the vinyl-pyridine or -pyrazine derivative is subjected to alkoxybromination with an N-bromo-amide or N-bromo-imide in the presence of an alcohol $R_1OH$, in agreement with the definition of $R_1$.

In the second stage, the derivative obtained is subjected to the aforesaid condensation reaction with the amine V ($NHR_2R_3$), in the presence of an organic solvent and sodium carbonate, by heating under reflux.

Pharmaceutically acceptable salts of the compounds of formula I are the acid addition salts obtained by reaction of the free base with a pharmaceutically acceptable organic or inorganic acid, such as HCl, HBr, acetic acid, phosphoric acid, methanesulphonic acid, maleic acid, fumaric acid, succinic acid, tartaric acid etc.

By alkyl in the definition of $R_1$ and $R_3$ is meant an alkyl group with 1 to 5 carbon atoms, such as methyl, ethyl, propyl, tert.butyl, sec.butyl and pentyl.

The activity of the compounds according to the invention, in particular the antibronchoconstrictory activity, has been demonstrated by way of pharmacological tests, the protocols of which are summarised below.

The antibronchoconstrictory activity was investigated on tricoloured guinea pigs according to the technique of Konzett and Rossler. The animals are anaesthetised with ethylcarbamate and, after tracheotomy, are artificially respirated at constant volume; whereby the intratracheal pressure is recorded continuously. Histamine (5 $\mu g.kg^{-1}$, i.v.) is administered before and at various time-intervals after treatment with the substance to be studied. The activity of the product administered intravenously is evaluated by comparing the amplitudes of the bronchospasms before and after treatment and calculating the percentage variation and the duration of action. The results are shown in Table I.

TABLE I

| Compound No.* | Dose (mg, i.v.) | % Inhibition of Bronchospasm | Duration in minutes |
| --- | --- | --- | --- |
| 1 | 5 | 56.5 | >60 |
| 2 | 0.05 | 85 | >120 |
| 3 | 5 | 50 | >15 |
| 6 | 0.025 | 90 | >120 |
| 7 | 0.25 | 97 | >60 |
| 8 | 0.1 | 95 | >15 |
| 9 | 0.25 | 98 | 30 |
| 10 | 1 | 100 | >60 |
| 11 | 0.25 | 100 | >60 |
| 12 | 0.5 | 91 | >60 |
| 14 | 5 | 82 | 45 |
| 15 | 0.05 | 80 | 60 |
| 16 | 0.1 | 79 | 45 |

*The "Compound No." refers to the numbering of the various compounds mentioned in Table II.

These results show that the compounds of the invention have interesting antibronchoconstrictory properties. In particular, the compounds No. 2, 6, 7, 8, 15 and 16 and especially the compound No. 6 show an excellent activity from a view point of both the intensity of the activity as well as the duration of action. The latter compound (No. 6) turned out to have an $ED_{50}$ value in this test of 0,0019 mg/kg bodyweight, thus being extremely potent.

The antibronchoconstrictory properties of the present compounds are, moreover, confirmed in other usual tests for this activity.

The pharmacological studies also showed that the compounds according to the invention did not possess a significant toxicity; the $LD_{50}$, p.o., on mice is between 300 and 800 $mg.kg^{-1}$.

The compounds of the formula I and their pharmaceutically acceptable salts can thus be used for example in the treatment of spastic bronchitis, chronic respiratory insufficiencies, respiratory allergies and for pulmonary function examination.

Together with usual pharmaceutical excipients, the compounds according to the invention can be administered to human beings in daily doses of between 1 and 100 mg and preferably between 10 and 100 mg, dependent on the mode of administration.

Preferred modes of administration are the oral administration and the administration by injection. The vehicle or excipient should of course be chosen according to the intended mode of administration. Galenical formulation of compositions according to the invention does not present difficulties and is effected in a manner known to those skilled in the art. Two examples of galenical formulation have been described below, merely by way of illustration.

A suitable tablet composition consists of:
Compound No. 6: 4 mg
Lactose: 80 mg
Corn starch: 12.5 mg
Polyvidone K 30: 3 mg
Magnesium stearate: 0.5 mg In order to prepare a batch of 1,000 tablets, the required amounts of Compound No. 6, lactose and corn starch are mixed and the mixture is moistened with a solution of polyvidone. When the mixture is homogeneous, granules are extruded and dried, the magnesium stearate is added and the mixture is pressed to obtain tablets having an average weight of 100 mg.

A composition for injection may consist of:
Compound No. 6: 3 mg
Propane-1,2-diol: 1.5 ml
Glucose: 250 mg
Water ppi q.s.: 5 ml In order to prepare a batch of 2 liters compound No. 6 is dissolved in propane-1,2-diol and glucose is dissolved in part of the water, then the two solutions are combined and the volume is made up to 2 liters.

The solution thus obtained is then filtered over a 0.22 $\mu m$ cellulose acetate membrane and filled into 5.15 ml ampoules.

EXAMPLE 1

1-[2-Methoxy-2-(6-methyl-3-pyridyl)-ethyl]-4-phenyl-piperazine 1. 154.5 g Of N-bromoacetamide were added gradually to a flask containing 1 liter of methanol, with stirring, the temperature being maintained at 0° C., and 133.2 g of 2-methyl-5-vinyl-pyridine were than added, stirring being continued until the temperature returned to room temperature.

When the reaction had ended, the 2-methyl-5-(1-methoxy-2-bromo)-ethyl-pyridine was distilled in vacuo. The oil obtained was then purified in the customary manner and redistilled over sodium carbonate. 150 g Of product of boiling point b.p.$_{0.5}$ 94° C. were obtained.

2. 16.1 g (0.07 mole) Of 2-methyl-5-(1-methoxy-2-bromo)-ethyl-pyridine and 9.4 g of N-phenylpiperazine dissolved in 50 ml of butanol were introduced into a flask equipped with a condenser.

9.4 Of sodium carbonate were added and the mixture was refluxed for 30 hours. The end of the reaction was monitored by thin layer chromatography. After removal of the sodium carbonate by filtration, the title product was left to crystallise in ethanol. After recrystallisation from ethyl acetate, 7.2 g of the title product were obtained; melting point 93° C.

EXAMPLE 2

1-[2-Methoxy-2-(6-methyl-3-pyridyl)-ethyl]-4-(2-methoxy-phenyl)-piperazine and fumarate salt In an analogous way as described in Example 1, 2-methyl-5-(1-methoxy-2-bromo)-ethyl-pyridine was prepared and was then reacted with 2-methoxy-phenyl-piperazine, in butanol as the solvent, in the presence of sodium carbonate. Starting from 16.1 g (0.07 mole) of the bromine derivative and 11.1 g (0.058 mole) of 2-methoxy-phenyl-piperazine in 50 ml of butanol in the presence of 12 g of sodium carbonate, and after heating under reflux for 21 hours, 10 g of the title product were obtained; melting point 88° C.

The free base was converted into a salt by the action of fumaric acid; a crystalline product of melting point 153° C. was obtained.

EXAMPLE 3

1-[2-Isobutoxy-2-(6-methyl-3-pyridyl)-ethyl]-4-(2-methoxy-phenyl)-piperazine a. 41.4 g Of N-bromoacetamide were gradually added to a flask containing 300 ml of isobutanol, with stirring, the temperature being maintained at 0° C., and 35.7 g of 2-methyl-5-vinyl-pyridine were then added, stirring being continued until the temperature returned to room temperature.

The reaction mixture was then left at room temperature for 48 hours and the bromine derivative formed was distilled. 87.4 g Of product, which was used in the next stage, were obtained.

b. 23.6 g (0.1 mole) of the bromine derivative obtained above and 15 g (0.08 mole) of 2-methoxy-phenyl-piperazine were reacted in 100 ml of butanol in the presence of 15 g of sodium carbonate, the reaction mixture being kept under reflux for 10 hours and the end of the reaction being monitored by thin layer chromatography. After removal of the carbonate by filtration and evaporation of the butanol to dryness, fumaric acid was added in order to obtain 2.2 g of the difumarate of the title compound with a melting point of 144° C.

EXAMPLE 4

N-[2-methoxy-2-(6-methyl-3-pyridyl)]-ethyl-tert.-butylamine 23 g Of the appropriate bromine derivative and 21.9 g of tert.-butylamine in 200 ml of butanol were condensed in the presence of 50 g of potassium carbonate, after which the free base thus obtained was converted with fumaric acid to give the title compound in the form of the fumarate (1:1.5) salt; melting point 221,6° C.

EXAMPLE 5

1-[2-Methoxy-2-(3-methyl-2-pyrazinyl)-ethyl]-4-phenyl-piperazine fumarate salt 12.7 g Of N-bromoacetamide were added to a mixture of 90 ml of methanol and 11 g of 2-methyl-3-vinyl-pyrazine, the temperature being kept between 0° C. and −5° C. The reaction mixture was then allowed to return to room temperature. The bromine derivative was extracted and purified to give 10 g of the appropriate bromo derivative; boiling point 99° C. (0,4 mm).

In the second stage, 2-methyl-3-(1-methoxy-2-bromo)-ethyl-pyrazine was subjected to a condensation reaction with phenyl-piperazine.

Starting from 10 g of the above bromine derivative, 7 g of the phenyl-piperazine, 100 ml of butanol and 10 g of potassium carbonate, 10 g of the title compound were obtained using the method described in Example 1 and were crystallised in the form of the fumarate; melting point 157° C.

In the same manner as described in Example 1 the following compounds were prepared:

TABLE II

| COMPOUND No. |  | $R_1$ | $-N\begin{array}{c}R_2\\R_3\end{array}$ | CRYSTALLINE FORM | MELTING POINT |
| --- | --- | --- | --- | --- | --- |
| 1 |  | —CH$_3$ |  | Fumarate | 159° C. |
| 2 |  | —CH$_3$ |  | Trihydrochlorate | 234° C. |

TABLE II-continued $$\text{CH}_3\text{-pyridine(X)-CH(CR}_1\text{)-CH}_2\text{-N(R}_2\text{)(R}_3\text{)}$$

| COMPOUND No. | CH₃–pyridine(X)– | R₁ | –N(R₂)(R₃) | CRYSTALLINE FORM | MELTING POINT |
|---|---|---|---|---|---|
| 3 | 2-methylpyridin-5-yl | $-CH_3$ | morpholino | Fumarate | 152° C. |
| 4 (Example 3) | 2-methylpyridin-5-yl | $-CH_2-CH(CH_3)_2$ | 4-(2-ethoxyphenyl)piperazin-1-yl | Difumarate | 144° C. |
| 5 | 2-methylpyridin-5-yl | $-CH_3$ | 4-(3-trifluoromethylphenyl)piperazin-1-yl | Difumarate | 155° C. |
| 6 (Example 1) | 2-methylpyridin-5-yl | $-CH_3$ | 4-phenylpiperazin-1-yl | Base | 93° C. |
| 7 (Example 2) | 2-methylpyridin-5-yl | $-CH_3$ | 4-(2-methoxyphenyl)piperazin-1-yl | Base | 86° C. |
| 8 | 2-methylpyridin-5-yl | $-CH_3$ | 4-(2-ethoxyphenyl)piperazin-1-yl | Base | 71° C. |
| 9 | 6-methylpyrazin-3-yl | $-CH_3$ | 4-phenylpiperazin-1-yl | Base | 63° C. |
| 10 | 2-methylpyridin-5-yl | $-C_2H_5$ | 4-phenylpiperazin-1-yl | Trihydrochlorate | 201.5° C. |
| 11 | 2-methylpyridin-5-yl | $-C_2H_5$ | 4-(2-methoxyphenyl)piperazin-1-yl | Base | 73° C. |
| 12 | 6-methylpyrazin-3-yl | $-CH_3$ | 4-(4-fluorophenyl)piperazin-1-yl | Base | 79.5° C. |

TABLE II-continued

| COMPOUND No. | ![ring] | R₁ | -N(R₂)(R₃) | CRYSTALLINE FORM | MELTING POINT |
|---|---|---|---|---|---|
| 13 (Example 4) | 2,3-dimethylpyridin-5-yl | —CH₃ | —NH—C(CH₃)₃ | fumarate (1; 1,5) | 221.6° C. |
| 14 (Example 5) | 2-methylpyrazin-5-yl (3-methylpyrazin) | —CH₃ | piperazinyl-phenyl | Fumarate | 157° C. |
| 15 | 2-methylpyridin-5-yl | —CH₃ | piperazinyl-(2,4-dimethoxyphenyl) | Trihydrochlorate monohydrate | 226° C. |
| 16 | 2-methylpyridin-5-yl | —CH₃ | piperazinyl-(2-methylphenyl) | Trihydrochlorate | 204° C. |
| 17 | 2-methylpyridin-5-yl | —CH₃ | piperazinyl-(3-chlorophenyl) | Liquid base | |
| 18 | 2-methylpyridin-5-yl | —CH₃ | piperazinyl-pyrimidin-2-yl | Liquid base | |
| 19 | 2-methylpyridin-5-yl | —CH₃ | piperazinyl-(4-chlorophenyl) | Liquid base | |

We claim:
1. A compound of the formula

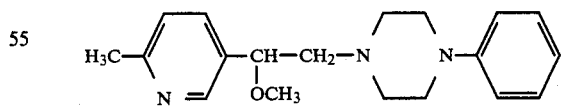

and the pharmaceutically acceptable salts thereof.

2. An antibronchospasmodic composition comprising as the active ingredient, an antibronchospasmodic amount of a compound according to claim 1, the pharmaceutically acceptable salts and mixtures thereof, and a pharmaceutically acceptable carrier.

* * * * *